United States Patent [19]

Ross et al.

[11] Patent Number: 5,252,593
[45] Date of Patent: Oct. 12, 1993

[54] PYAZOLE CONTAINING BENZOFURAN DERIVATIVES AND PHARMACEUTICAL COMPOSITIONS

[75] Inventors: Barry C. Ross; David Middlemiss; David I. C. Scopes; Torquil I. M. Jack; Kevin S. Cardwell; Michael D. Dowle; Colin D. Eldred; John G. Montana; Pritom Shah; Stephen P. Watson, all of Ware, Great Britain

[73] Assignee: Glaxo Group Limited, Greenford, United Kingdom

[21] Appl. No.: 883,380

[22] Filed: May 15, 1992

[30] Foreign Application Priority Data

May 16, 1991 [GB] United Kingdom ............... 9110623

[51] Int. Cl.$^5$ ................ A61K 31/41; A61K 31/415; C07D 405/02; C07D 405/14
[52] U.S. Cl. ................... 514/382; 514/406; 548/252; 548/364.4
[58] Field of Search .............. 548/252, 364.4; 514/382, 406

[56] References Cited

U.S. PATENT DOCUMENTS 5,183,825 2/1993 Kees .................... 548/364.4

FOREIGN PATENT DOCUMENTS 0434429 6/1991 European Pat. Off. .
0446062 9/1991 European Pat. Off. .
0449699 10/1991 European Pat. Off. .
WO91/15479 10/1991 PCT Int'l Appl. .

Primary Examiner—Robert W. Ramsuer
Attorney, Agent, or Firm—Bacon & Thomas

[57] ABSTRACT

The invention provides compounds of formula (I):

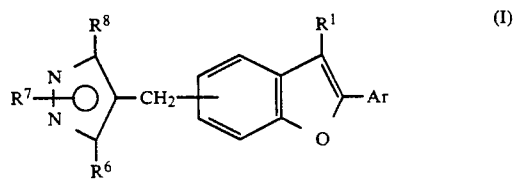

or a physiologically acceptable salt, solvate or metabolically labile ester thereof The compounds may be used in the treatment or prophylaxis of hypertension and diseases associated with cognitive disorders.

20 Claims, No Drawings

PYAZOLE CONTAINING BENZOFURAN DERIVATIVES AND PHARMACEUTICAL COMPOSITIONS

This invention relates to benzofuran derivatives, processes for their preparation and pharmaceutical compositions containing them. According to a first aspect of the invention we provide a compound of the general formula (I):

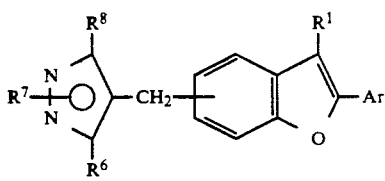

or a physiologically acceptable salt, solvate (e.g. hydrate) or metabolically labile ester thereof in which
$R^1$ represents a hydrogen atom or a halogen atom or a group selected from $C_{1-6}$alkyl, $C_{2-6}$alkenyl, fluoro$C_{1-6}$alkyl, $C_{1-6}$alkoxy, —CHO, —$CO_2H$ or —$COR^2$;
Ar represents the group

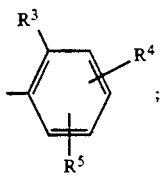

$R^2$ represents a group selected from $C_{1-6}$alkyl, $C_{2-6}$alkenyl, $C_{1-6}$alkoxy or the group —$NR^{14}R^{15}$;
$R^3$ represents a group selected from —$CO_2H$, —$NHSO_2CF_3$ or a C-linked tetrazolyl group;
$R^4$ and $R^5$ which may be the same or different each independently represent a hydrogen atom or a halogen atom or a $C_{1-6}$alkyl group;
$R^6$ represents a hydrogen atom or a group selected from $C_{1-6}$alkyl or $C_{2-6}$alkenyl, $C_{1-6}$alkylthio, $C_{1-6}$alkoxy, $C_{3-7}$cycloalkyl or $C_{3-7}$cycloalkyl$C_{1-4}$alkyl;
$R^7$ represents a hydrogen atom or a group selected from $C_{1-6}$alkyl, $C_{3-7}$cycloalkyl, $C_{3-7}$cycloalkyl$C_{1-4}$alkyl, $C_{3-6}$alkenyl, fluoro$C_{1-6}$alkyl, fluoro$C_{3-6}$alkenyl, phenyl, —$(CH_2)_kCOR^9$ or —$(CH_2)_kSO_2R^9$;
$R^8$ represents a hydrogen atom or a group selected from $C_{1-6}$alkyl optionally substituted by a hydroxy or $C_{1-6}$alkoxy group, $C_{2-6}$alkenyl, fluoro$C_{1-6}$alkyl, —$(CH_2)_mR^{10}$, —$(CH_2)_nCOR^{11}$ or —$(CH_2)_pNR^{12}COR^{13}$;
$R^9$ represents a group selected from $C_{1-6}$alkyl, $C_{2-6}$alkenyl, $C_{1-6}$alkoxy or the group —$NR^{14}R^{15}$;
$R^{10}$ represents a phenoxy or benzyloxy group;
$R^{11}$ represents a hydrogen atom or a group selected from hydroxy, $C_{1-6}$alkyl, $C_{1-6}$alkoxy, phenyl, phenoxy or the group —$NR^{14}R^{15}$;
$R^{12}$ represents a hydrogen atom or a $C_{1-6}$alkyl group;
$R^{13}$ represents a hydrogen atom or a group selected from $C_{1-6}$alkyl, $C_{1-6}$alkoxy, phenyl, benzyl, phenoxy or the group —$NR^{14}R^{15}$;
$R^{14}$ and $R^{15}$, which may be the same or different, each independently represent a hydrogen atom or a $C_{1-4}$alkyl group or —$NR^{14}R^{15}$ forms a saturated heterocyclic ring which has 5 or 6 ring members and may optionally contain in the ring one oxygen atom;
k represents zero or an integer from 1 to 4;
m represents an integer from 1 to 4;
n represents zero or an integer from 1 to 4; and
p represents an integer from 1 to 4.

Where the compound of general formula (I) is optically active, said formula (I) is intended to cover all enantiomers, diastereoisomers and mixtures thereof including racemates. Where a compound of the present invention contains one or more double bonds, these may exist in the cis or trans configuration. Furthermore, where such geometric isomers exist, formula (I) is intended to cover mixtures thereof.

The invention also includes within its scope the solvates, especially the hydrates of compounds of general formula (I).

Within the above definition the term 'alkyl' or 'alkoxy' as a group or part of a group means that the group is straight or branched. The term 'alkenyl' as a group or part of a group means that the group is straight or branched and contains at least one carbon-carbon double bond. The term 'cycloalkyl' as a group or part of a group may be, for example, a cyclopropyl, cyclobutyl, cyclopentyl or cyclohexyl group.

The term 'halogen' means a fluorine, chlorine, bromine or iodine atom.

The term 'fluoro$C_{1-6}$alkyl' or 'fluoro$C_{3-6}$alkenyl' means a $C_{1-6}$alkyl or $C_{3-6}$alkenyl group in which one or more hydrogen atoms have been replaced by a fluorine atom, for example, —$CH_2CF_3$ or —$CH=CHCF_3$.

Within the above definition when —$NR^{14}R^{15}$ represents a saturated heterocyclic ring, this contains 5 or 6 ring members, one of which may be an oxygen atom. Suitable heterocyclic groups are a pyrrolidino, piperidino or morpholino group.

A preferred class of compounds of general formula (I) is that wherein $R^6$ represents a hydrogen atom or a $C_{1-5}$alkyl, or a $C_{3-5}$alkenyl group. Particularly preferred are those compounds wherein $R^6$ is a $C_{2-4}$alkyl group (especially an ethyl, n-propyl or n-butyl group).

Another preferred class of compounds of the general formula (I) is that wherein the group $R^7$ is a group selected from $C_{1-6}$alkyl, preferably $C_{1-5}$alkyl, especially ethyl, isopropyl or isobutyl; $C_{3-7}$cycloalkyl, preferably $C_{3-5}$cycloalkyl, especially cyclobutyl; $C_{3-7}$cycloalkyl$C_{1-4}$alkyl, preferably $C_{3-5}$cycloalkyl$C_{1-4}$alkyl, especially cyclopropylmethyl; phenyl; fluoro$C_{1-6}$alkyl, preferably fluoro$C_{1-3}$alkyl, especially —$CH_2CF_3$; and —$(CH_2)_kSO_2R^9$ where $R^9$ represents the group —$NR^{14}R^{15}$ (in which $R^{14}$ and $R^{15}$ each represent a $C_{1-4}$alkyl group) and k is zero.

A further preferred class of compounds of general formula (I) is that wherein the group $R^7$ is adjacent to the group $R^8$.

Yet another preferred class of compounds of general formula (I) is that wherein $R^8$ is selected from a hydrogen atom; or a group selected from $C_{1-6}$alkyl, preferably $C_{1-3}$alkyl, optionally substituted by hydroxy or $C_{1-3}$alkoxy, especially methoxy; or —$(CH_2)_mR^{10}$, especially wherein $R^{10}$ is a benzyloxy group and m is 1 or 2; or —$(CH_2)_nCOR^{11}$, especially wherein $R^{11}$ represents hydrogen hydroxy or $C_{1-3}$alkoxy, especially methoxy, and n is zero, 1 or 2 especially zero or 1; or —$(CH_2)_pNR^{12}COR^{13}$, especially wherein $R^{12}$ represents hydrogen or a $C_{1-3}$alkyl group, $R^{13}$ represents hydrogen or a $C_{1-3}$alkyl group, and p is 1 or 2. In particular, $R^8$ may represent a group selected from —$CH_2OH$, $CH_2OCH_3$, —CHO or —$CO_2H$.

A yet further preferred class of compounds of general formula (I) is that wherein $R^1$ represents a hydrogen atom or a halogen atom or a group selected from $C_{1-6}$alkyl, $C_{1-6}$alkoxy or fluoro$C_{1-6}$alkyl, and in particular a halogen atom, especially bromine.

Preferably, in the compounds of general formula (I), the pyrazolylmethyl moiety is attached at the 5- or 6-position on the benzofuran ring, and especially the 5-position.

Conveniently, in the compounds of general formula (I), $R^4$ and $R^5$ may each independently represent a hydrogen atom or a halogen atom. In particular $R^4$ and $R^5$ each represent hydrogen atoms.

The physiologically acceptable acid addition salts of the compounds of formula (I) may be derived from inorganic or organic acids. Examples of such salts include hydrochlorides, hydrobromides, sulphates, phosphates, benzoates, methanesulphonates or trifluoroacetates.

The compounds may also form salts with suitable bases. Examples of such salts are alkali metal (e.g. sodium or potassium), alkaline earth metal (e.g. calcium or magnesium), ammonium and substituted ammonium (e.g. dimethylammonium, triethylammonium, 2-hydroxyethyldimethylammonium, piperazinium, N,N-dimethylpiperazinium, tetraethylammonium, piperidinium, ethylenediammonium and choline).

it will be appreciated that, for pharmaceutical use, the salts referred to above will be physiologically acceptable, but other salts may find use, for example, in the preparation of the compounds of general formula (I) and the physiologically acceptable salts thereof.

It will be further appreciated that the compounds of general formula (I) may be chemically modified in the form of compounds which in vivo (for example, by enzymic attack) will provide the parent compounds of general formula (I). Such prodrugs may be, for example, physiologically acceptable metabolically labile ester derivatives. These may be formed by esterification, for example of any of the carboxylic acid groups in the parent compound of general formula (I), with prior protection of any other reactive groups present in the molecule. Examples of such esters include lower alkyl esters (e.g. methyl or ethyl esters), alkenyl esters (e.g. vinyl or alkyl esters), alkynyl esters(e.g. ethynyl or propynyl esters), alkoxyalkyl esters, (e.g. methoxymethyl or 2-methoxyethyl esters), alkylthioalkyl esters (e.g. methylthiomethyl esters) haloalkyl esters (e.g. 2-iodoethyl or 2,2,2-trichloroethyl esters), alkanoyloxyalkyl esters (e.g. acetoxymethyl, 1-acetoxyethyl or pivaloyloxymethyl esters), alkoxycarbonyloxyalkyl esters (e.g. 1-ethoxycarbonyloxyethyl or 1-methoxycarbonyloxyethyl esters), aroyloxyalkyl esters (e.g. benzoyloxymethyl or 1-benzoyloxyethyl esters), substituted or unsubstituted aralkyl esters (e.g. benzyl or 4-amidobenzyl esters), substituted or unsubstituted aminoalkyl esters (e.g aminoethyl or 2-N,N-dimethylaminoethyl esters) or hydroxyalkyl esters (e.g. 2-hydroxyethyl or 2,3-dihydroxypropyl esters).

In addition to the above ester derivatives the present invention includes within its scope compounds of general formula (I) in the form of other physiologically acceptable equivalents, i.e. physiologically acceptable compounds which, like the metabolically labile esters, are converted in vivo into the parent compounds of general formula (I).

According to a second aspect of the present invention we provide a compound of general formula (I) or a physiologically acceptable salt, solvate or metabolically labile ester thereof for use in therapy.

In particular, the compounds of the present invention may be used in the treatment or prophylaxis of hypertension (for example, essential, malignant or resistant, caused by oral contraceptives, coarctation of the aorta or renal vascular disease) and pulmonary hypertension.

The compounds of the present invention may also be used in the treatment or prophylaxis of congestive heart failure, acute or chronic heart failure, aortic or cardiac insufficiency, post-myocardial infarction, renal insufficiency and renal failure (for example, as a result of diabetic nephropathy, glomerular nephritis, scleroderma or renal crisis), proteinuria, Bartter's syndrome, secondary hyperaldosteronism, Reynaud's syndrome, cerebrovascular insufficiency, peripheral vascular disease, diabetic retinopathy, atherogenesis and for the improvement of vascular compliance.

They are also potentially useful for the treatment of cognitive disorders such as dementia (e.g. Alzheimer's disease) and other CNS disorders, such as anxiety disorders, schizophrenia, depression and alcohol or drug (e.g. cocaine) dependency.

According to a further aspect of the present invention we provide a compound of general formula (I) or a physiologically acceptable salt, solvate or metabolically labile ester thereof for use in the treatment of the aforementioned diseases, especially hypertension.

According to another aspect of the present invention we provide a compound of general formula (I) or a physiologically acceptable salt, solvate or metabolically labile ester solvate thereof for the manufacture of a therapeutic agent for the treatment of the aforementioned diseases, especially hypertension.

According to a further aspect of the present invention we provide a method of treating the aforementioned diseases, especially hypertension, which method comprises administering an effective amount to a patient in need of such treatment of a compound of general formula (I) or a physiologically acceptable salt, solvate or metabolically labile ester thereof.

It will be appreciated that the compounds of general formula (I) or a physiologically acceptable salt, solvate, or metabolically labile ester thereof may advantageously be used in conjunction with one or more other therapeutic agents, such as for example diuretics and/or different antihypertensive agents such as $\beta$-blockers, calcium channel blockers or ACE inhibitors. It is to be understood that such combination therapy constitutes a further aspect of the present invention.

It will be further appreciated that reference herein to treatment extends to prophylaxis as well as to the treatment and relief of established symptoms.

While it is possible that a compound of general formula (I) may be administered as the raw chemical it is preferable to present the active ingredient as a pharmaceutical formulation.

The compounds of general formula (I) and their physiologically acceptable salts, solvates and metabolically labile esters may be formulated for administration in any convenient way, and the invention also includes within its scope pharmaceutical compositions comprising at least one compound of general formula (I) or a physiologically acceptable salt, solvate or metabolically labile ester thereof adapted for use in human or veterinary medicine. Such compositions may be presented for use in conventional manner in admixture with one or more physiologically acceptable carriers or excipients.

The carrier(s) must be 'acceptable' in the sense of being compatible with the other ingredients of the formulation and not deleterious to the recipient thereof.

Thus, the compounds according to the invention may be formulated for oral, buccal, parenteral or rectal administration or in a form suitable for administration by inhalation or insufflation. Oral administration is preferred.

Tablets and capsules for oral administration may contain conventional excipients such as binding agents, for example mucilage of starch or polyvinylpyrrolidone; fillers, for example, lactose, microcrystalline cellulose or maize-starch; lubricants, for example, magnesium stearate or stearic acid; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, ciucose/sugar syrup or carboxymethyl cellulose; emulsifying agents, for example, sorbitan monooleate; non-aqueous vehicles (which may include edible oils), for example, propylene glycol or ethyl alcohol; and preservatives, for example, methyl or propyl p-hydroxybenzoates or sorbic acid. The compounds or their salts or esters may also be formulated as suppositories, e.g. containing conventional suppository bases such as cocoa butter or other glycerides. For buccal administration the composition may take the form of tablets or lozenges formulated in conventional manner.

It will be appreciated that both tablets and capsules may be manufactured in the form of sustained release formulations, such that they provide a controlled continuous release of the compounds according to the invention over a period of hours.

The compounds of general formula (I) and their physiologically acceptable salts, solvates and metabolically labile esters may be formulated for parenteral administration by bolus injection or continuous infusion and may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoro methane, dichlorotetrafluoroethane or other suitable gas. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges of e.g. gelatin, or blister packs from which the powder may be administered with the aid of an inhaler or insufflator.

The pharmaceutical formulations according to the invention may also contain other active ingredients such as antimicrobial agents, or preservatives.

It will be appreciated that the amount of a compound of general formula (I) required for use in treatment will vary not only with the particular compound selected but also with the route of administration, the nature of the condition being treated and the age and condition of the patient and will ultimately be at the discretion of the attendant physician or veterinarian. In general, however, when the compositions comprise dosage units, each unit will preferably contain 5 mg to 500 mg, advantageously where the compounds are to be administered orally 25 mg to 400 mg of the active compound. The daily dosage as employed for adult human treatment will preferably range from 5 mg to 3 g, most preferably from 25 mg to 1 g which may be administered in 1 to 4 daily doses.

The compounds of the invention may be prepared by a number of processes as described below wherein the various groups are as defined for general formula (I) unless otherwise specified.

It will be appreciated by a person skilled in the art that where necessary, reactive or labile groups in the following processes may be protected in a conventional manner using, for example, one of the groups described in process (C) hereinafter.

Thus, according to a further aspect of the present invention we provide a process (A) for preparing the compounds of general formula (I) which comprises treating a compound of general formula (II)

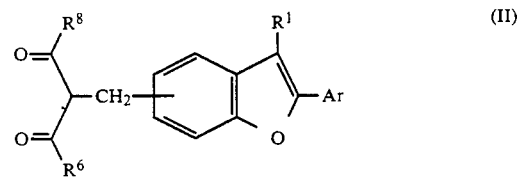

(wherein $R^1$, $R^6$, $R^8$ and Ar are as defined in general formula (I)) with a hydrazine of formula (III)

$$R^7NHNH_2 \qquad (III)$$

(wherein $R^7$ is as defined in general formula (I)) followed by the removal of any protecting groups where present, as described hereinafter.

The reaction is preferably effected in a solvent such as an aqueous alcohol e.g. ethanol, an ether e.g tetrahydrofuran or dioxan, a substituted amide e.g dimethylformamide, acetonitrile or water at a temperature in the range of 0° C. to reflux and preferably at room temperature.

The intermediate diketones of formula (II) are novel compounds and form a further aspect of the invention.

In another general process (B) a compound of general formula (I) may be obtained by interconversion of another compound of general formula (I). Thus for example, when $R^7$ represents a hydrogen atom, such a compound may be converted into a compound of general formula (I) wherein $R^7$ represents a group $-(CH_2)_kCOR^9$ or $-(CH_2)_kSO_2R^9$ by reaction with $L-(CH_2)_kCOR^9$ or $L-(CH_2)_kSO_2R^9$, respectively (wherein L represents a leaving group, for example, a halogen atom such as a chlorine, bromine or iodine, or a hydrocarbylsulphonyloxy group such as methanesulphonyloxy, or p-toluenesulphonyloxy). The reaction is conveniently effected in a suitable solvent such as a substituted amide e.g. dimethylformamide or an ether e.g. tetrahydrofuran in the presence of a base such as sodium hydride or sodium amide, at a temperature in the range 0° C. to reflux, and preferably at room temperature.

In an alternative example of process (B) a compound of general formula (I) wherein $R^7$ represents a hydrogen atom may be converted into a compound of general formula (I) wherein $R^7$ represents a $C_{1-6}$alkyl, $C_{3-7}$cycloalkyl or $C_{3-7}$cycloalkyl$C_{1-4}$alkyl group, or a group $-(CH_2)_kCOR^9$ or $-(CH_2)_kSO_2R^9$ where k is 1 to 4, by reaction with a corresponding alkylating agent, for example, an alkylhalide such as an alkyliodide. The reaction is conveniently effected in a suitable solvent such as a substituted amide e.g. dimethylformamide or an ether e.g. tetrahydrofuran in the presence of a base such as potassium carbonate or sodium hydride, at a temperature in the range of 0° C. to reflux, and preferably at room temperature.

It will also be appreciated that other substituents in a compound of general formula (I) may be modified by techniques well known in the art to produce alternative compounds of general formula (I).

In another general process (C) a compound of general formula (I) may be obtained by deprotection of a protected intermediate of general formula (Ia)

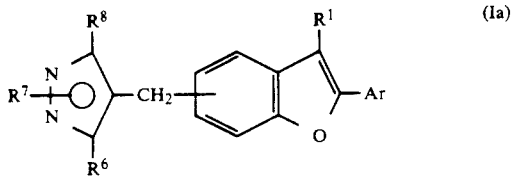

(wherein $R^1$, $R^6$, $R^7$, $R^8$ and Ar are as defined in general formula (I) except that at least one reactive group is blocked by a protecting group). The protecting groups may be any conventional protecting groups, for example as described in "Protective Groups in Organic Synthesis" by Theodora Greene (John Wiley and Sons Inc., 1981). Examples of carboxyl protecting groups include $C_{1-6}$alkyl such as methyl or t-butyl, or $C_{7-10}$aralkyl such as benzyl.

When $R^3$ in the group Ar is a tetrazolyl group, this may be protected with, for example, the trityl group -C(phenyl)$_3$, or a p-nitrobenzyl or 1-ethoxyethyl group.

Deprotection to yield the compound of general formula (I) may be effected using conventional techniques. Thus, for example, aralkyl groups may be cleaved by hydrogenolysis in a suitable organic solvent such as an alcohol, e.g. ethanol, in the presence of a transition metal catalyst such as palladium or an oxide thereof on a support such as charcoal, and conveniently at room temperature and pressure. Carboxyl protecting groups such as alkyl groups may be cleaved by hydrolysis Using a base such as an alkali metal hydroxide (e.g. sodium hydroxide or potassium hydroxide) in a suitable solvent (e.g. an aqueous alcohol such as methanol or ethanol) at any suitable temperature up to reflux or, in the case of a t-butyl group, by acid hydrolysis. Deprotection of the tetrazolyl group when protected with a trityl group may be effected by acid hydrolysis using trifluoroacetic acid, a sulphonic acid such as d110-camphor sulphonic acid, or a mineral acid such as hydrochloric acid in a suitable solvent such as methanol, ethanol, tetrahydrofuran or mixtures thereof conveniently at room temperature to reflux. Alternatively, when possible, deprotection of the tetrazolyl group can be effected by catalytic hydrogenation as previously described.

In another general process (D) a compound of general formula (I) in which the substituent $R^3$ in the group Ar represents a C-linked tetrazolyl group, may also be prepared from a compound of general formula (IV)

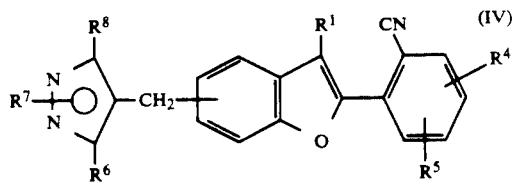

(wherein, $R^1$, $R^4$, $R^5$, $R^6$, $R^7$ and $R^8$ are as defined in general formula (I)) by reaction with a suitable azide such as sodium azide, ammonium azide (preferably prepared in situ from sodium azide and ammonium chloride), trialkyl-(e.g.triethyl)ammonium azide (preferably prepared in situ from sodium azide and a trialkylamine salt (e.g. triethylamine hydrochloride)), a trialkylsilylazide (e.g. trimethylsilylazide) or a tri-alkyl tin azide e.g. tributyl tin azide. The reaction is conveniently effected in a solvent such as xylene, an ether, for example, dimethoxyethane or tetrahydrofuran, or a substituted amide, for example, dimethylformamide, at an elevated temperature, such as the reflux temperature of the solvent, for between 1 and 10 days. Where the azide is tributyl tin azide the reaction may conveniently be effected in the absence of a solvent at a temperature between room temperature and 180° C. such a reaction leaves the tetrazolyl group protected with a tributyl tin group, which can readily be removed using aqueous base or acid. Where aqueous base is used to effect this deprotection, the compound may be treated with an aqueous acid to liberate the tetrazole.

Compounds of general formula (IV) may be prepared by processes analogous to those described herein commencing from a compound of formula (XVII).

The Intermediate compounds of general formula (IV) are novel compounds and form a further aspect of the present invention.

In another general process (E) a compound of general formula (I) in which the substituent $R^3$ in the group Ar represents $-NHSO_2CF_3$, may be prepared from a compound of general formula (V)

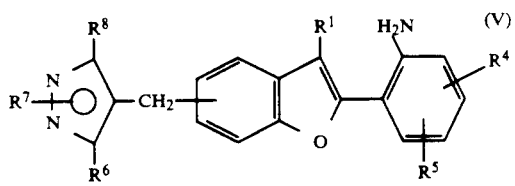

(wherein $R^1$, $R^4$, $R^5$, $R^6$, $R^7$ and $R^8$ are as defined in general formula (I)) by reaction with trifluoromethanesulphonic anhydride or trifluoromethylsulphonyl chloride, in a suitable solvent such as a halogenated hydrocarbon, e.g. dichloromethane or chloroform in the presence of a base, e.g. triethylamine.

Compounds of general formula (V) may be prepared by processes analogous to those described herein conmencing from a compound of formula (XII) wherein $R^{3a}$ represents an amino group or a nitro precursor thereof.

Alternatively, compounds of general formula (V) may be prepared by a Curtius rearrangement of a compound of formula (I) wherein $R^3$ is —$CO_2H$ (provided that this is the only unprotected carboxylic acid group in the molecule) using, for example, diphenylphosphorylazide in the presence of a base such as triethylamine and in a solvent such as an alcohol (e.g. tert-butanol) to form a carbamate followed by deprotection of the amine in a conventional manner, for example by acid hydrolysis using hydrochloric acid in a solvent such as ethanol.

The intermediate compounds of general formula (V) and their acid addition salts are novel compounds and form a further aspect of the present invention.

In another general process (F) a compound of general formula (I) wherein $R^8$ represents the group —$(CH_2)_n COR^9$ where n is zero and $R^9$ is $C_{1-6}$alkoxy, may be prepared by reacting a compound of formula (VI)

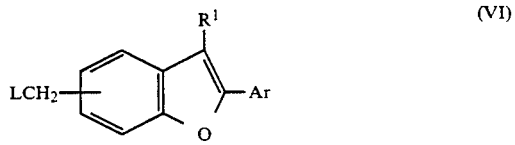
(VI)

(wherein $R^1$ and Ar are as defined in general formula (I) and L is a leaving group as defined above) with a compound of formula (VII)

(VII)

(wherein $R^6$ and $R^7$ are as defined in general formula (I) and $R^{9a}$ is a $C_{1-6}$alkoxy group).

The reaction is conveniently effected at a temperature between $-100°$ C. and room temperature in a suitable solvent such as an ether, for example, tetrahydrofuran, dimethoxyethane or diethyl ether.

In another general process (G), a compound of general formula (I) wherein $R^7$ is adjacent to the group R may be prepared by reacting a compound of formula (XXI)

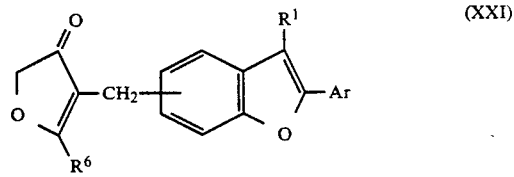
(XXI)

(wherein $R^1$, $R^6$ and Ar are as defined in general formula (I)) with a hydrazine of formula (III) as defined above.

The reaction is preferably effected in a solvent such as acetonitrile, an aqueous alcohol e.g. ethanol, an ether e.g. tetrahydrofuran or a substituted amide e.g. dimethylformamide, at a temperature in the range of 0° C. to the reflux temperature of the solvent.

It will be appreciated that the product of the reaction between a compound of formula (XXI) and a hydrazine of formula (III) will be a compound of formula (I) wherein $R^8$ is the group —$CH_2OH$. This group may be modified by conventional techniques, for example, by a stepwise oxidation to a compound of general formula (I) wherein $R^8$ represents the group —CHO or —$CO_2H$ using, for example, manganese dioxide, chromium trioxide in pyridine, or tetra-n-propylammonium perruthenate (TPAP) with 4-methyl morpholine-N-oxide to produce the aldehyde, and sodium chlorite with sodium dihydrogen orthophosphate, or potassium permanganate or chromic acid in the presence of acid to produce the carboxylic acid.

The compounds of formula (XXI) are novel and represent a further aspect of the present invention.

In the processes (A),(B), (C), (D), (E), (F) and (G) described above, the compounds of general formula (I) may be obtained in the form of a salt, conveniently in the form of a physiologically acceptable salt. Where desired, such salts may be converted into the corresponding free acids or free bases using conventional methods.

Physiologically acceptable salts of the compounds of general formula (I) may be prepared by reacting a compound of general formula (I) with an appropriate acid or base in the presence of a suitable solvent such as acetonitrile, acetone, chloroform, ethyl acetate or an alcohol, e.g. methanol, ethanol or isopropanol.

Physiologically acceptable salts may also be prepared from other salts, including other physiologically acceptable salts, of the compounds of general formula (I), using conventional methods.

The intermediate compounds of general formula (II) may be prepared from a compound of formula (VIII)

(VIII)

(wherein $R^6$ and $R^8$ are as defined in general formula (I)) by condensation with a compound of formula (VI).

The reaction is preferably effected under basic conditions, for example, in the presence of sodium hydride, potassium carbonate or sodium methoxide. The reaction is conveniently effected in a solvent such as acetonitrile or an ether e.g. tetrahydrofuran or dioxan, or a substituted amide e.g. dimethylformamide, at a temperature between 0° C. and the reflux temperature of the solvent.

Compounds of formula (VIII) may be prepared by reaction of a compound of formula (IX)

$R^6COCH_3$  (IX)

With a compound of formula (X)

$R^8CO_2CH_3$  (X)

preferably in the presence of a base such as sodium amide, sodium hydride or tetra-n-butyl ammonium fluoride. The reaction is conveniently effected in a solvent such as an ether e.g. tetrahydrofuran or dioxan, or a halogenated hydrocarbon e.g. dichloromethane at a temperature between 0° C. and the reflux temperature of the solvent.

Compounds of formula (VI) may be prepared from a compound of formula (XI)

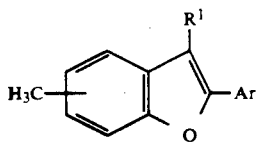

using any suitable reagent well known in the art for converting the methyl group in formula (XI) into the group —CH$_2$L (wherein L is as defined above). Thus for example, when L is a halogen atom, a compound of formula (XI) can be converted into a compound of formula (VI) using N-chloro amides, tert-butyl hypochlorite or N-bromosuccinimide. Halogenation may be catalysed by light, thus the reaction mixture can be illuminated with a suitable artificial light source, and preferably in the presence of a free radical initiator such as azobisisobutyronitrile (AIBN) or dibenzoyl peroxide. The reaction may be conveniently effected in a solvent such as a halogenated hydrocarbon, e.g. carbon tetrachloride at an elevated temperature such as the reflux temperature of the solvent.

Compounds of formula (VI) or (XI) wherein R$^1$ is a halogen atom, for example, a bromine atom, may be prepared by halogenation of a compound of formula (VI) or (XI), respectively, wherein R$^1$ represents a hydrogen atom, using, for example, bromine, in a suitable solvent such as a halogenated hydrocarbon, e.g. carbon tetrachloride.

Compounds of formula (XI) in which R$^3$ in the group Ar represents a C-linked tetrazolyl group may be prepared from a precursor of a compound of formula (XI) wherein the substituent R$^3$ represents a nitrile group using the reagents and conditions described in process (D).

Compounds of formula (XI) in which R$^3$ in the group Ar represents the group —NHSO$_2$CF$_3$ may be prepared from a compound of formula (XI) wherein the substituent R$^3$ represents and amino group using the reagents and conditions described in process (E).

Compounds of formula (XI) in which R$^3$ represents —COOH or —NHSO$_2$CF$_3$, and the cyano and amino precursors described above may be prepared by reaction of a compound of formula (XII)

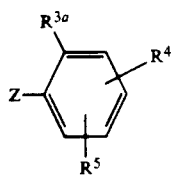

(wherein Z represents a bromine or iodine atom or the group —OSO$_2$CF$_3$, and R$^{3a}$ represents either —COOH, —NHSO$_2$CF$_3$, a nitrile or amino group or a group convertible thereto by standard methodology) with a compound of formula (XIII)

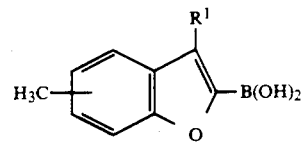

in the presence of a palladium (O) compound such as tetrakis(triphenylphosphine)palladium (O) in a solvent such as dimethoxyethane in the presence of a base such as sodium carbonate or thallium hydroxide. The reaction is conveniently effected at an elevated temperature, such as the reflux temperature of the solvent.

Compounds of formula (XIII) may be prepared by reaction of a compound of formula (XIV)

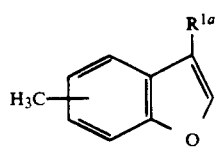

(wherein R$^{1a}$ represents a hydrogen atom or a group selected from C$_{1-6}$alkyl or C$_{2-6}$alkenyl) with an alkyl lithium compound such as n-butyl lithium at a reduced temperature, for example, between −100° C. and 0° C. in a solvent such as an ether (e.g. tetrahydrofuran), followed by treatment with a tri-alkylborate such as triisopropylborate during which the temperature is conveniently brought up to room temperature. Subsequently water may be added and the mixture treated with a mineral acid such as sulphuric acid thus producing a compound of formula (XIII).

Compounds of formula (VII) may be prepared by lithiation of a compound of formula (XV)

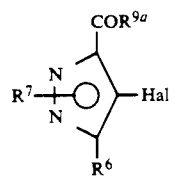

The reaction may be effected using an alkyllithium compound, for example, tert-butyl lithium at a temperature between −100° C. and room temperature, in a suitable solvent such as an ether, for example, tetrahydrofuran, dimethoxyethane or diethyl ether.

Compounds of formula (XV) may be prepared by halogenation of a compound of formula (XVI)

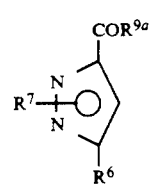

using standard methodology described herein above.

Compounds of formula (XVI) may be prepared by the reaction of a compound of formula (VIII) wherein R$^8$ represents —(CH$_2$)$_n$COR$^9$ (where n is zero and R$^9$ is C$_{1-6}$alkoxy) with a compound of formula (III) using the method of general process (A).

Intermediates of formula (XII) where $R^{3a}$ represents a C-linked tetrazolyl group may be prepared from a compound of formula (XVII)

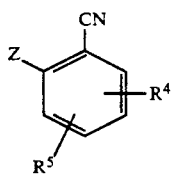
(XVII)

(followed where necessary by protection of any reactive groups), using methods well-known in the art such as those described in process (D).

Intermediates of formula (XII) wherein $R^{3a}$ represents —$NHSO_2CF_3$ may be prepared from a compound of formula (XVIII)

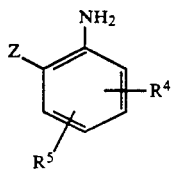
(XVIII)

(followed where necessary by the protection of any reactive group) using methods well known in the art such as those described in process (E).

Compounds of formula (XI) may also be prepared by a reaction of a compound of formula (XIX)

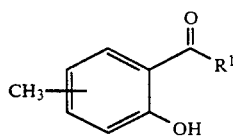
(XIX)

wherein $R^1$ is as previously defined with the exception of CHO and $COR^2$, where $R^2$ is $C_{1-6}$alkoxy or —$NR^{14}R^{15}$, and halogen) with a suitably substituted benzene of formula (XX)

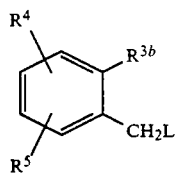
(XX)

(wherein L is as previously defined and $R^{3b}$ is as defined for $R^{3a}$ in formula (XII) with the exception of —$CO_2H$ and —$NHSO_2CF_3$) in the presence of a base such as sodium hydride or potassium carbonate. The formation of the compound of formula (XI) is a two step reaction which requires up to one equivalent of base per step. It will be appreciated however that the reaction can be effected in the presence of two equivalents of base to avoid the need to isolate the intermediate. The reaction is conveniently effected in a solvent such as an ether e.g. tetrahydrofuran, an alcohol e.g. ethanol or a substituted amide e.g. dimethylformamide, at a temperature between room temperature and the reflux temperature of the solvent.

Compounds of formula (XXI) may be prepared, for example, by the deprotection and cyclisation of a compound of formula (II) in which $R^8$ represents the group —$CH_2OY$ (wherein Y represents a hydroxyl protecting group, for example, an alkyl ether such as a t-butyl ether, an optionally substituted benzyl ether such as a benzyl or p-methoxybenzyl ether or a silyl ether such as a t-butyldimethylsilyl or t-butyldiphenylsilyl ether).

Other suitable hydroxyl protecting groups, their method of formation and suitable means of deprotection are described in Chapter 2 of "Protective Groups in Organic Synthesis" (2nd Edition) by T. W. Greene and P. G. M. Wuts, John Wiley & Sons, Inc. New York (1991).

Thus, for example, the above protecting groups may be removed under conditions of acid hydrolysis using a mineral acid such as hydrochloric acid, basic hydrolysis using a base such as sodium hydroxide, or using fluoride ions (in the case of the silyl ethers) or by catalytic hydrogenation (in the case of the benzyl ethers) using hydrogen in the presence of a catalyst such as Raney nickel, platinum or palladium.

Particularly preferred protecting groups are silyl ethers, especially t-butyldimethylsilyl (TBDMS) ethers, especially where the compound of formula (II) contains other protected reactive groups, for example, where $R^3$ in the group Ar is a protected derivative of —$CO_2H$, a protected derivative of —$NH_2$ or a protected derivative of a C-linked tetrazolyl group. Removal of a silyl ether protecting group in such compounds, without affecting the protecting group in $R^4$, may be effected using the basic fluoride ion from, for example, tetrabutylammoniumfluoride (TBAF) in tetrahydrofuran, or aqueous hydrogen fluoride in acetonitrile. Both of these deprotection reactions conveniently take place at room temperature.

Intramolecular cyclisation of the hydroxymethyl diketone formed by the deprotection is preferably effected without isolation of the hydroxymethyl diketone intermediate. cyclisation is promoted by mild acid catalysis using, for example, dilute acid, e.g. hydrochloric acid or even silica gel.

It will be appreciated that compounds of formula (XI) in which $R^1$ represents a hydrogen or halogen atom may also be converted into compounds of formula (XI) in which $R^1$ represents the group methyl (via hydrogenolysis of the Mannich base), —CHO or —$COR^2$ (wherein $R^2$ is as defined in general formula (I)) using techniques well known in the art, such as those described in "Heterocyclic Chemistry" by J. A. Joule and G. F. Smith, Van Nostrand Reinhold Company, London (1972), "Heterocyclic Chemistry" by A. Albert, 2nd Edition, The Athlone Press, London (1968), "Heterocyclic Compounds", Vol. 29 by A. Mustafa, John Wiley and Sons Inc., New York (1974), "Heterocyclic Compounds", Vol. 2 by R. C. Elderfield, John Wiley and Sons Inc., New York (1951) and "Advances in Heterocyclic Chemistry", Vol. 29 by A. R. Katritsky and A. J. Boulton, Academic Press, New York (1981).

Intermediates of formulae (III), (IX), (X), (XII), (XIV), (XVII), (XVIII), (XIX) and (XX), are either known compounds or may be prepared by methods analogous to those used for the preparation of the known compounds.

The following examples illustrate the invention. Temperatures are in °C. "Dried" refers to drying using magnesium sulphate. Thin layer chromatography (T.l.c.) was carried out over silica and column chromatography was carried out on silica (Merck 9385 unless otherwise stated), using one of the following solvent systems: A-ether:hexane, B-ether: petroleum ether, C- dichloromethane:ethanol, D-dichloromethane:ether, E-ether:acetic acid, F-ether:hexane:methanol:acetic acid, G-ether:petroleum ether:acetic acid. The following abbreviations are used: THF-tetrahydrofuran; DME-dimethoxyethane; AIBN-azobisisobutyronitrile; DMF-dimethylformamide; TMEDA-tetramethylethylenediamine; NBS-N-bromosuccinimide; DMAP-4-dimethylaminopyridine; DEAD-diethyl azodicarboxylate.

Intermediate 1

5-Methylbenzofuran-2-boronic acid n-Butyl lithium (35.16 ml) was added dropwise to a stirred solution of TMEDA (9.58 ml) and 5-methylbenzofuran (8.22 g) in ether (250 ml) maintaining the temperature below −60° C. throughout. The solution was warmed to about −10° C. over 45 minutes and stirred at this temperature for 30 minutes. A precipitate formed on warming. The suspension was cooled and triisopropylborate (43 ml) was added, maintaining the temperature below −60° C. The solution was warmed gradually to room temperature before quenching with 2N HCl (70 ml). The mixture was extracted with ether (3×50 ml) and the combined organic extracts washed with 2N HCl (4×30 ml), water (2×30 ml) and dried before evaporation to give the title compound as an orange solid (12.75 g).

T.l.c. System A (1:1), Rf 0.3.

Intermediate 2

2-(5-Methyl-2-benzofuranyl)benzonitrile

Intermediate 1 (20 g) was added to a stirred solution of 2-bromobenzonitrile (10.34 g) and tetrakistriphenylphosphine palladium (0) (1.5 g) in DME (200 ml) and 8% NaHCO$_3$ solution (50 ml) at reflux under nitrogen. Further catalyst (1.5 g) was added and the reaction continued overnight. The reaction was cooled to room temperature and diluted with ether (200 ml). The organic layer was separated, washed with water (3×100 ml) and dried. Filtration and evaporation gave a white solid which was purified by chromatography eluting with system A (1:9) to give the title compound (10.58 g) as a white solid.

T.l.c. System A (1:9), Rf 0.45.

Intermediate 2 was also prepared by the alternative two-step reaction:

a) 2-Hydroxy-5-methylbenzaldehyde p-Cresol (100 g) in dry THF(100 ml) was added dropwise to a mechanically stirred, freshly prepared solution of ethyl magnesium bromide [magnesium (25.0 g) and bromoethane (75 ml)] in THF (500 ml) under nitrogen at a rate which maintained a slow reflux (about 30 mins). After a further 30 mins toluene (1.21) was added, followed by 1,3-dimethyl-3,4,5,6-tetrahydro-2(1H)-pyrimidone (125 ml), and paraformaldehyde (70 g). The mixture was then heated at reflux for 16 h. The mixture was concentrated by distillation and aqueous hydrochloric acid (2M, 600 ml) then added. Water (600 ml) was added and the mixture filtered through "hyflo". The organic phase was separated, dried, filtered and concentrated in vacuo to give a brown oil. The oil was steam distilled and the product extracted from the distillate with ether (1 liter). The organic extract was dried, filtered and concentrated in vacuo to give a pale yellow slurry which was cooled to −10° C., triturated with ether (precooled to −78° C., 100 ml), filtered off rapidly and washed with ether (precooled to −78° C.) to give the title compound as colourless needles, (131.4 g).

T.l.c. System A (1:5) Rf 0.5.

b) 2-(5-Methyl-2-benzofuranyl)benzonitrile

A solution of the product of step (a) (130 g) in dry DMF (400 ml) was added dropwise to a solution of sodium methoxide (56.2 g) in ethanol (400 ml) mechanically stirred under nitrogen. After a further 20 mins, a solution of 2-(bromomethyl)benzonitrile (182.2 g) in dry DMF (400 ml) was added dropwise. The mixture was then heated to 75° C. for 30 min. The solution was allowed to cool for 1 h. A slurry of sodium methoxide (56.2 g) in dry DMF (100 ml) was added and the mixture heated at reflux for 1.5 h. The mixture was concentrated in vacuo and then poured into iced water. The solid was collected, and then triturated with methanol to give the title compound (Intermediate 2) as a beige solid (149.4 g).

T.l.c. System A (1:9) Rf 0.4.

Intermediate 3

5-[2-(5-Methyl-2-benzofuranyl)phenyl]-1H-tetrazole

A suspension of Intermediate 2 (94 g) in tri-n-butyl tin azide (268 g) was heated at 100°-125° C. for 1.25 h under nitrogen. The resulting solution was then heated at 155°-160° C. for 2 h under nitrogen, then poured into a solution of aqueous sodium hydroxide (0.8N, 3070 ml). This solution was extracted with ether. The aqueous phase was acidified to pH 1 with 5N hydrochloric acid and the resulting precipitate filtered, washed with water and dried under vacuum. The solid was dissolved in ethyl acetate, washed with brine and dried. The solvent was evaporated to give the title compound as a buff-coloured solid (100.3 g).

T.l.c. System A (1:1), Rf 0.2.

Intermediate 4

5-[2-(3-Bromo-5-methyl-2-benzofuranyl)phenyl]-1H-tetrazole

A solution of bromine (58 g), in carbon tetrachloride (140 ml) was added dropwise over 35 min to a mechanically stirred solution of Intermediate 3 (50 g) in dry dioxan (2090 ml) at room temperature under nitrogen. The resulting solution was stirred at room temperature for 3 h, then cyclohexene (63 ml) was added. Another preparation of the product was carried out simultaneously on the same scale as described above, and at this stage they were combined. The solvent was evaporated and the residual brown oil (260 g) partitioned between ether and aqueous sodium hydroxide. The alkaline solution was acidified to pH 1 with hydrochloric acid, then extracted with ethyl acetate. The combined ethyl acetate extracts were washed with brine, dried and evaporated to give a buff solid (125 g) which was triturated under hot toluene, cooled and filtered off to give the title compound as a cream coloured solid (101.8 g).

T.l.c. Ether/petroleum ether/acetic acid (50:50:1), Rf 0.27.

Intermediate 5

5-[2-(3-Bromo-5-methyl-2-benzofuranyl)phenyl]-2-(triphenylmethyl)-2H-tetrazole Triethylamine (57.4 g) was added to a mechanically stirred suspension of Intermediate 4 (101 g) in dry dichloromethane (2.9 liters) at room temperature under nitrogen. Triphenylmethyl chloride (79.3 g) followed by DMAP (1.0 g) were added at room temperature and the mixture stirred for 3 h under nitrogen. The reaction mixture was washed with water, then brine and dried. The solvent was filtered and concentrated to a volume of about 1.2 liters then filtered through silica (Merck 9385, 14 cm diam. column). Elution with dichloromethane gave a colourless solid (158.4 g) which was triturated with ether and filtered to give the title compound as a colourless solid (147.9 g).

T.l.c. (Dichloromethane/hexane 1:1), Rf 0.28

Intermediate 6

5-[2-[3-Bromo-5-(bromomethyl)-2-benzofuranyl]-phenyl]-2-(triphenylmethyl)-2H-tetrazole Intermediate 5 (74 g) was dissolved in carbon tetrachloride (2050 ml) by heating the suspension to reflux. The resulting colourless solution was allowed to cool to 50° C. then NBS (22.1 g) was added, followed by benzoyl peroxide (1.1 g). The reaction mixture was heated at reflux for 3.25 h,, under nitrogen, then allowed to cool to room temperature. The reaction mixture was washed with water then brine. Another preparation of the product was carried out simultaneously on the same scale as described above, and at this stage they were combined and dried. The solvent was evaporated to give a colourless solid (168 g) which was triturated with ether/methanol (1:1) and filtered to give the title compound as a colourless solid (160.8 g).

T.l.c. (Dichloromethane/hexane 1:1), Rf 0.15.

Intermediate 7

Ethyl 2,4-dioxooctanoate

A mixture of ethyl oxalate (97.21 g) and hexan-2-one (66.58 g) was added dropwise to a solution of sodium ethoxide (50.1 g) in ethanol (160 ml) at reflux. The resultant mixture was heated at reflux for 2 h. The cooled reaction mixture was poured into a stirring mixture of ice (500 g) and water (100 ml) and the resultant slurry adjusted to pH 1.5(conc.$H_2SO_4$). The two layers were separated and the bottom layer extracted with toluene (2×200 ml). The combined organics were washed with brine (200 ml), dried and concentrated in vacuo to give a residue (107 g) which was purified by distillation to afford the title compound as a colourless liquid (67.2 g). b.p. (0.3 mmHg) 96° C.

Intermediate 8

Ethyl 3-butyl-1H-pyrazole-5-carboxylate

Hydrazine hydrate (85%; 3.8 g), was added dropwise to a solution of Intermediate 7 (20 g) in ethanol (150 ml) at room temperature under nitrogen. The mixture was stirred overnight at room temperature, the solvent was then evaporated in vacuo and the residue purified by flash column chromatography eluting with System B (1:2) and increasing the polarity to (1:1) to give the title compound as a pale yellow oil (12.4 g)

T.l.c System B (1:1) Rf 0.25

Intermediate 9a and 9b (a) Ethyl 3-butyl-1-ethyl-1H-pyrazole-5-carboxylate;
(b) Ethyl 5-butyl-1-ethyl-1H-pyrazole-3-carboxylate A solution of Intermediate 8 (5.0 g) in dry DMF (10 ml) was added dropwise to a suspension of sodium hydride (60% dispersion in mineral oil; 1.325 g; mineral oil removed by washing with petroleum ether (3×15 ml)) in dry DMF (50 ml) at 0° under nitrogen. The mixture was stirred at 0°-5° for 10 mins, then a solution of ethyl iodide (2 ml) in dry DMF (5 ml) was added dropwise at 0° over 5 mins. The mixture was allowed to warm to room temperature and stirred for 2 h. The mixture was partitioned between water (150 ml) and ethyl acetate (3×75 ml). The combined organic extracts were washed with brine/water (1:1) (3×100 ml) and dried. The solvent was evaporated to give a pale yellow oil (4.93). The crude material was purified by flash column chromatography eluting with System B (1:1) to give Intermediate 9a as a colourless oil (1.86 g)

Tlc System B (1:1) Rf 0.8; and

Intermediate 9b as a colourless oil (2.46 g)

T.l.c. System B (1:1) Rf 0.25

Intermediate 10

3-Butyl-1-ethyl-1H-pyrazole-5-carboxylic acid

Sodium hydroxide (0.41 g) in water (1 ml) was added dropwise to a solution of Intermediate 9a (1.85 g), in ethanol (25 ml) at room temperature under nitrogen. The solution was heated under reflux for 1 h, then cooled and concentrated in vacuo. Water (20 ml) was added and the solution acidified to pH 1 with dilute hydrochloric acid (2N; 5 ml), then extracted with ethyl acetate (3×25 ml). The combined organic extracts were washed with brine (1×25 ml) and dried. The solvent was evaporated to give the title compound as a colourless solid (1.51 g)

Tlc System E (100:1) Rf 0.65

Intermediate 11

4-Bromo-3-butyl-1-ethyl-1H-pyrazole-5-carboxylic acid

Bromine (1.25 g) in carbon tetrachloride (3 ml) was added dropwise to a solution of Intermediate 10 (1.5 g) in dry dioxan (20 ml) at room temperature under nitrogen. The mixture was stirred overnight at room temperature. Cyclohexene (2 ml) was added and the solvent evaporated in vacuo. The residue was purified by flash column chromatography on silica gel eluting with ether/petroleum ether/acetic acid 50:50:1 to give the title compound as a fawn-coloured solid (1.5 g)

T.l.c. System G (50:50:1) Rf 0.5.

Intermediate 12

4-[[3-Bromo-2-[2-[2-(triphenylmethyl)-2H-tetrazol-5-yl]phenyl]-5-benzofuranyl]methyl]-3-butyl-1-ethyl-1H-pyrazole-5-carboxylic acid A solution of Intermediate 11 (0.2 g) in dry THF (3 ml) was added dropwise over 1 minute to a suspension of sodium hydride (32 mg; 60% dispersion in oil) in THF (4 ml) at 0° under nitrogen. The mixture was stirred at 0° for 5 mins, then cooled to −78° and t-butyl lithium (1.7M; 0.852 ml) added dropwise over 5 mins and the mixture stirred at −78° for 40 mins. A solution of Intermediate 6 (588 mg), in THF (20 ml) was added dropwise over 10 mins and the mixture allowed to warm to room temperature over 4 h. The resulting pale yellow solution was partitioned between saturated ammonium chloride solution (20 ml) and ethyl acetate (3×20 ml). The combined organic extracts were washed with brine (1×30 ml) and dried. The solvent was evaporated and the residue purified by flash column chromatography on silica (sorbsil C60;). Elution with ether/petroleum ether/acetic acid (50:50:1) gave the title compound as a colourless solid (21 mg)

T.l.c. System G (50:50:1) Rf 0.8.

Intermediate 13

3-[[3-Bromo-2-[2-[2(triphenylmethyl)-2H-tetrazol-5-yl]phenyl]-5-benzofuranyl]methyl]-1-(methoxy)-2,4-octanedione A solution of 1-methoxy-2,4-octanedione (1.53 g), in dry THF (20 ml) was added dropwise to a suspension of sodium hydride (391 mg, 60% dispersion mineral oil, removed by trituration in hexane) in dry THF (10 ml) over 5 mins at 0° under nitrogen. The mixture was stirred at room temperature for 30 mins. A solution of Intermediate 6 (6 g), in dry dichloromethane (50 ml) was added dropwise over 5 mins at room temperature. The mixture was heated under reflux for 72 h, cooled and the solvent evaporated in vacuo. The residue was partitioned between ether (3×50 ml) and water (50 ml). The combined organic extracts were washed with brine (5 ml), and dried and concentrated in vacuo to give a pale yellow gum (7 g). The crude material was purified by flash column chromatography eluting with System B (1:1) to give the title compound as a colourless foam (1.787 g)

T.l.c. System B (1:1) Rf 0.25.

Intermediates 14a and 14b (14a)
5-[2-[3-Bromo-5-[[3-butyl-5-(methoxymethyl)-1-(2,2,2-trifluoroethyl)-1H-pyrazol-4-yl]methyl]-2-benzofuranyl]phenyl]-2-(triphenylmethyl)-2H-tetrazole; and (14b)
5-[2-[3-Bromo-5-[[5-butyl-3-(methoxymethyl)-1-(2,2,2-trifluoroethyl)-1H-pyrazol-4-yl]methyl]-2-benzofuranyl]phenyl]-2-(triphenylmethyl)-2H-tetrazole 2,2,2-Trifluoroethylhydrazine (70% in water; 0.115 g) in ethanol (2 ml) was added to a solution of Intermediate 13 (555 mg) in ethanol (15 ml) and dichloromethane (5 ml). The mixture was stirred at room temperature for 18 h. A further portion of the hydrazine (0.115 g) was added and the mixture warmed at 60° for 4 h. The solvent was evaporated and the residue purified by short-path column chromatography on silica gel eluting with System B (1:1) to give Intermediate 14a as a colourless foam (190 mg)

Tlc System B (1:1) Rf 0.45; and
Intermediate 14b as a colourless foam (213 mg)
Tlc System B (1:1) Rf 0.2

Intermediate 15

3-[[3-Bromo-2-[2-[2-(triphenylmethyl)-2H-tetrazol-5-yl]phenyl]-5-benzofuranyl]methyl]-1-(phenylmethoxy)-2,4-octanedione A solution of 1-(phenylmethoxy)-2,4-octanedione (200 mg) in tetra n-butylammonium fluoride (1M in THF 0.854 ml) was heated at 80° C. under vacuum for 1 h. The resultant solvate was cooled, dissolved in dichloromethane (10 ml) and then Intermediate 6 (1.15 g) was added and the resultant solution stirred at room temperature for 16 h. The reaction mixture was concentrated in vacuo and then purified by flash column chromatography eluting with a gradient of System B (1:9 →1:3) to afford the title compound as a white solid (270 mg)

n.m.r. (250 MHz, CDCl$_3$)δ0.9–1.4(7H,m), 2.2(1H,dt), 2.4(1H,dq) 3.1(1H,dd), 3.3(1H,dd), 3.9(2H,s), 4.2(1H,t), 4.45(2H,s), 6.7–7.8(26H,m), 8.2(1H,dd).

Intermediate 16

1,1-Dimethylethyl 2-(3-bromo-5-methyl-2-benzofuranyl)benzoate

The title compound was prepared from Intermediate 1 and 1,1-dimethylethyl 2-bromobenzoate according to the method of Intermediate 2, followed by bromination according to the method of Intermediate 4.

T.l.c. System G (1:2) Rf=0.3

Intermediate 17

1,1-Dimethylethyl 2-[3-bromo-5-(bromomethyl)-2-benzofuranyl]benzoate

The title compound was prepared from Intermediate 16 according to the method of Intermediate 6.

T.l.c. System A (1:10) Rf=0.4

Intermediate 18

1-(Phenylmethoxy)-hexane-2,4-dione

2-Butanone (32.7 ml) in dry THF (120 ml) was added to lithium diisopropylamide (1.5M in THF; 250 ml) at −78° C. Methyl benzyloxyacetate (30,0 g) was added with stirring and the mixture allowed to warm to room temperature and was then heated at 45° overnight. After cooling the reaction was quenched with saturated ammonium chloride solution, acidified and extracted with ether (3×100 ml). After drying and evaporation, the title compound was obtained as a brown oil (45.6 g).

T.l.c. System B (1:9) Rf=0.25

Intermediate 19

1,1-Dimethylethyl 2-[3-bromo-5-[3-oxo-2-[(phenylmethoxy)]acetyl]pentyl]-2-benzofuranyl]benzoate A solution of Intermediate 18 (3.15 g) in dry THF (10 ml) was added dropwise to a suspension of sodium hydride (60%; 0.57 g) in THF (50 ml) at 0° under nitrogen. The mixture was allowed to warm to room temperature and stirred for 30 min at room temperature. The resulting solution was added dropwise to a solution of Intermediate 17 and potassium iodide (2.37 g) in dry THF (40 ml) at 45° over 15 min and the mixture warmed at 55° for 4 h. The solution was cooled to room temperature, the solvent evaporated and the residue partitioned between saturated ammonium chloride solution (100 ml) and ethyl acetate (3×75 ml). The combined organic extracts were washed with brine (1×100 ml) and dried. The solvent was evaporated to give a colourless gum (12 g), which was purified by flash column chromatography eluting with System A (1:4) to give the title compound as a colourless foam (6.61 g).

T.l.c. System A (1:4) Rf 0.2

Intermediate 20

1,1-Dimethylethyl 2-[3-bromo-5-[[3-ethyl-5-[(phenylmethoxy)methyl]-1H-pyrazol-4-yl]methyl]-2-benzofuranyl]benzoate Hydrazine hydrate (0.6 ml) was added to a solution of Intermediate 19 (6.61 g) in ethanol (100 ml) containing dichloromethane (20 ml) at 5° under nitrogen. The mixture was allowed to warm to room temperature and stirred for 18 h. A further portion of hydrazine hydrate (0.3 ml) was added and stirring continued for 6 h. The solvent was evaporated in vacuo and the residue purified by flash column chromatography eluting with System A (7:3) to give the title compound as a colourless foam (5.18 g).

T.l.c. System B (4:1) Rf 0.2

Intermediate 21

1,1-Dimethylethyl 2-[3-bromo-5-[[1,3-diethyl-5[(phenylmethoxy) methyl]-1H-pyrazol-4-yl]methyl]-2-benzofuranyl]benzoate A solution of Intermediate 20 (6.54 g) in dry DMF (20 ml) was added dropwise to a suspension of sodium hydride (60%; 0.56 g) in dry DMF (30 ml) at 0° under nitrogen over 15 min. The mixture was stirred at 0°-5° for 30 min, then ethyl bromide (0.88 ml) was added in one portion and the mixture allowed to warm to room temperature over 2 h. The mixture was partitioned between saturated ammonium chloride solution (100 ml) and ethyl acetate (3×100 ml). The combined organic extracts were washed with brine (1×100 ml) and dried. The solvent was evaporated to give a pale yellow gum. The crude material was purified by flash column chromatography eluting with System A (3:7) to give the title compound as a colourless gum (2.90 g).

T.l.c. System B (4:1) Rf 0.65

Intermediate 22

1,1-Dimethylethyl 2-[3-bromo-5-[[1,3-diethyl-5-(hydroxymethyl)-1H-pyrazol-4-yl]methyl]-2-benzofuranyl]benzoate A solution of Intermediate 21 (2.815 g) in ethanol/acetic acid (4:1; 50 ml) was hydrogenated over prereduced palladium (5%; 50% paste with water; 280 mg) over 18 h at room temperature and pressure. The catalyst was filtered off and the filtrate evaporated to give a pale yellow foam which was dissolved in carbon tetrachloride (30 ml) containing acetic acid (5 ml). The solution was cooled to 0° and bromine in carbon tetrachloride (3.1 mM; 8.7 ml) added dropwise under nitrogen. The mixture was stirred for 2 h, the solvent was evaporated and the residue partitioned between ethyl acetate (3×50 ml) and aqueous sodium thiosulphate solution (10%; 50 ml). The combined organic extracts were washed with brine (1×100 ml) and dried. The solvent was evaporated to give a pale yellow foam which was purified by flash column chromatography eluting with System B (9:3) to give the title compound as a colourless foam (1.143 g).

T.l.c. ether Rf 0.6

Intermediate 23

1,1-Dimethylethyl 2-[3-bromo-5-[(1,3-diethyl-5-formyl-1H-pyrazol-4-yl)methyl]-2-benzofuranyl]benzoate Activated manganese dioxide (926 mg) was added to a solution of the Intermediate 22 (1.14 g) in dichloromethane/dioxan (2:1; 60 ml) and the mixture heated under reflux for 18 h. Further manganese dioxide (0.926 g) was added and refluxing continued for 18 h. More manganese dioxide (0.926 g) was added and refluxing continued for 16 h. The cooled mixture was filtered and evaporated to give a colourless gum (1.097 g) which was purified by flash column chromatography eluting with System B 1:1 and increasing the polarity to ether to give the title compound as a colourless gum (766 mg).

T.l.c. system B (1:1) Rf 0.45

Intermediate 24

4-[[3-Bromo-2-[2-[(1,1-dimethylethoxy)carbonyl]-phenyl]-5-benzofuranyl]methyl]-1,3-diethyl-1H-pyrazole-5-carboxylic acid A mixture of sodium chlorite (1.26 g) and sodium dihydrogen orthophosphate (1.26 g) in water (12 ml) was added in one portion to a vigorously stirred mixture of Intermediate 23 (756 mg), 2-methyl-2-butene (2M in THF; 7.8 ml) and tert-butanol (12 ml) in THF (30 ml) at room temperature. The mixture was vigorously stirred for 1 h, then partitioned between brine (50 ml) and ethyl acetate (3×30 ml). The combined organic extracts were washed with brine (1×50 ml) and dried. The solvent was evaporated to give the title compound as a colourless foam (921 mg).

T.l.c. ether Rf 0.75

Intermediate 25

1,1-Dimethylethyl 2-[5-[[5-(aminocarbonyl)-1,3-diethyl-1H-pyrazol-4-yl]methyl]-3-bromo-2-benzofuranyl]benzoate 1,1-Carbonyldiimidazole (478 mg) was added to a solution of Intermediate 24 (0.554 g) in dry THF (20 ml) at room temperature under nitrogen. The mixture was stirred for 2 h, then ammonia was bubbled into the solution for 10 min at −70°. The mixture was allowed to warm to room temperature, then partitioned between ethyl acetate (3×20 ml) and hydrochloric acid (0.5M; 30 ml). The combined organic extracts were washed with brine (1×50 ml) and dried. The solvent was evaporated to give the title compound as a colourless foam (528 mg)

T.l.c. ether Rf 0.5

Intermediate 26

1-[[(1,1-Dimethylethyl)dimethylsilyl]oxy]-2,4-hexanedione

2-Butanone (14.4 ml) in dry THF (20 ml) was added dropwise to a stirred solution of lithium diisopropylamide (1.5M solution in THF; 118 ml) in dry THF (20 ml) at −55° to −65° under nitrogen. The mixture was stirred at −65° for 30 min before dropwise addition of methyl [[(1-dimethylethyl)dimethylsilyl]oxy]acetate (16.3 g) in dry THF (20 ml) at −65° to −55°. The mixture was stirred at 45° for 16 h then added to saturated ammonium chloride solution (400 ml) and extracted with ether (3×250 ml). The combined organic extracts were washed with brine (3×100 ml), dried and concentrated in vacuo. The residue was purified by flash column chromatography eluting with 5% ether in hexane to afford the title compound, (7.2 g) as a brown oil.

T.l.c. System A (19:1) Rf=0.45

Intermediate 27

4-[[2-(2-Aminophenyl)-3-bromo-5-benzofuranyl]methyl]-5-ethyl-3(2H)-furanone

A solution of Intermediate 26, (14.2 g) in THF (50 ml) was added slowly to sodium hydride (60% dispersion in mineral oil; 2.6 g) in THF (80 ml). The mixture was stirred for 30 min before 1,1-dimethylethyl [2-[3-bromo-5-(bromomethyl)-2-benzofuranyl]phenyl]carbamate (described in European Patent Specification No. 0434 249A, published 26th Jun. 1991), (33.4 g) in THF (150 ml) was added over 15 min and the mixture stirred at 45° C. for 16 h. The mixture was added to water (1000 ml) and extracted with ether (3×800 ml). The combined organic extracts were washed with water (2×500 ml) and brine (2×500 ml), dried and concentrated in vacuo to afford 1,1-dimethylethyl [2-[3-bromo-5-[[1-[[(1,1-dimethylethyl) dimethylsilyl]oxy]-2,4-dioxo-3-hexyl]methyl]-2-benzofuranyl]phenyl]carbamate as a brown oil (47 g).

A solution of this oil and tetrabutylammoniumfluoride (1M solution in THF; 175 ml) in THF (400 ml) was stirred for 3 h. Ether (600 ml) was added and the solution washed with aqueous sodium bicarbonate (8%, 2×500 ml) and brine (2×500 ml). The organic phase was dried and concentrated in vacuo. The residue was mixed with dichloromethane and trifluoroacetic acid (40 ml) was added. The solution was stirred for 4 h then left to stand for 48 h, and then the solvent was removed in vacuo and ethyl acetate (600 ml) added. After washing with aqueous sodium bicarbonate (8%; 3×600 ml) the organic phase was dried and concentrated. Purification by flash column chromatography eluting with petroleum ether/dichloromethane/ether (3:2:0.5) afforded the title compound as a yellow foam (10.6 g).

T.l.c. petroleum ether/dichloromethane/ether (30:20:5) Rf=0.08

Intermediate 28

4-[[2-(2-Aminophenyl)-3-bromo-5-benzofuranyl]methyl]-1-butyl-3-ethyl-1H-pyrazole-5-methanol A solution of Intermediate 27 (5.0 g) and butylhydrazine (10 g) in THF (40 ml) was stirred at 70° C. for 72 h. Ether (150 ml) was added, the solution washed with brine/water (1:1; 3×150 ml), dried and concentrated in vacuo. The residue was purified by flash column chromatography eluting with 5% ether in dichloromethane to afford the title compound, (3.3 g) as a white foam.

T.l.c. System D (19:1) Rf=0.1

Intermediate 29

4-[[2-(2-Aminophenyl)-3-bromo-5-benzofuranyl]methyl]-1-butyl-3-ethyl-1H-pyrazole-5-carboxaldehyde A mixture of Intermediate 28 (4.8 g) and manganese dioxide (8.0 g) in THF was stirred under nitrogen at 75° C. for 48 h. The mixture was filtered through hyflo and the solvent removed in vacuo. The orange gum was purified by flash column chromatography eluting with System B (1:3) increasing in polarity to ether to afford the title compound, (2.7 g) as an orange gum.

T.l.c. System D (19:1) Rf=0.72

Intermediate 30

5-[2-[3-Bromo-5-[[3-butyl-5-(methoxymethyl)-1H-pyrazole-4-yl]methyl]-2-benzofuranyl]phenyl]-2-(triphenylmethyl)-2H-tetrazole A solution of hydrazine (85%; 22 mg) in ethanol (1 ml) was added to a solution of Intermediate 13 (305 mg) in ethanol (10 ml) containing dichloromethane (3 ml). The solution was stirred for 18 h at 24°. The solvent was evaporated in vacuo and the residue purified by short-path column chromatography on silica (Merck 7729; 6 g). Elution with ether gave the title compound as a colourless foam (0.2 g).

T.l.c. ether Rf=0.25

Example 1

3-Bromo-2-[2-(1H-tetrazol-5-yl)phenyl]-5-benzofuranyl]methyl]-3-butyl-1-ethyl-1H-pyrazole-5-carboxylic acid Conc. hydrochloric acid (1 drop) was added to a solution of Intermediate 12 (64 mg) in methanol (2 ml) at room temperature under nitrogen. The mixture was stirred at room temperature for 2 h, then concentrated (to about 0.25 ml), then purified by flash column chromatography elution with System G (75:25:1) to give a fawn coloured solid (40 mg) which was triturated under System B (1:5) and filtered to give the title compound as a fawn coloured solid (17 mg)

mp 168°–174°

T.l.c. System G (75:25:1) Rf 0.5.

Example 2

5-[2-[3-Bromo-5-[[3-butyl-5-(methoxymethyl)-1-(2,2,2-trifluoroethyl)-1H-pyrazol-4-yl]methyl]-2-benzofuranyl]phenyl]-1H-tetrazole dl-1-Camphor sulphonic acid (67 mg) was added to a solution of Intermediate 14a (268 mg) in methanol (5 ml) and dichloromethane (2 ml). The mixture was stirred at room temperature for 48 h. The solvent was evaporated and the residue purified by flash column chromatography eluting with System G (100:100:1) to give the title compound as a colourless foam (55 mg) after azeotroping with heptane to remove acetic acid.

T.l.c. System G (100:100:1) Rf 0.25

| Analysis Found: | C,54.7; H,4.7; N,13.0 |
|---|---|
| $C_{27}H_{26}BrF_3N_6O_2 0.25\ C_7H_{16}$ requires: | C,54.9; H,4.8; N,13.4% |

Similarly prepared was:

Example 3

5-[2-[3-Bromo-5-[[5-butyl-3-(methoxymethyl)-1-(2,2,2-trifluoroethyl)-1H-pyrazol-4-yl]methyl]-2-benzofuranyl]phenyl]-1H-tetrazole as a colourless foam (120 mg)

From a solution of the Intermediate 14b (210 mg) in methanol (3 ml) and dichloromethane (1 ml) with dl-1-camphor-sulphonic acid (52 mg).

T.l.c. System G (100:100:1) Rf 0.15

| Analysis Found: | C,53.3; H,4.3; N,13.1; |
|---|---|
| $C_{27}H_{26}BrF_3N_6O_2$ requires: | C,52.9; H,4.3; N,13.6% |

Examples 4a and 4b a)

5-[2-[3-Bromo-5-[[3-butyl-5-[(phenylmethoxy)methyl]-1-(2,2,2-trifluoroethyl)-1H-pyrazol-4-yl]methyl]-2-benzofuranyl]phenyl]-1H-tetrazole; and b)

5-[2-[3-Bromo-5-[[5-butyl-3-[(phenylmethoxy)methyl]-1-(2,2,2-trifluoroethyl)-1H-pyrazol-4-yl]methyl]-2-benzofuranyl]phenyl]-1H-tetrazole To a solution of Intermediate 15 (1.0 g) in ethanol (25 ml) and dichloromethane (8 ml) was added 2,2,2-trifluoroethylhydrazine (90% in water; 195 mg) and the resultant solution heated at reflux for 5 h. The solvent was removed in vacuo and the residue purified by flash column chromatography eluting with System B (1:4) graduating to system B (2:1)+2% acetic acid, to give:

Example 4a as a white solid (48 mg)

T.l.c. ether:petroleum ether:methanol:acetic acid (50:50:1:1) Rf =0.33 n.m.r (250 MHz, CDCl$_3$)δ0.95(3H,q), 1.2–1.8(4H,m), 2.48(2H,t), 3.90(2H,s), 4.45(2H,s), 4.51(2H,s), 4.7(2H,q), 7.0–7.3(8H,m), 7.7(2H,m), 7.8(1H,m), 8.1(1H,dd); and Example 4b as a white solid (50 mg)

I.r. (Nujol) 2200–3200, 1463, 1378, 1265, 1161 cm$^{31\ 1}$ n.m.r. (250 MHz, CDCl$_3$)δ0.9 (3H,q), 1.2–1.7(4H,m), 2.55(2H,t), 3.95(2H,s), 4.38(2H,s),4.45(2H,s), 4.6(2H,q) 7.0–7,4(8H,m),7.7(2H, m),7.82(1H,m), 8.15(1H,dd).

Example 5

4-[[3-Bromo-2-[2-(1H-tetrazol-5-yl)phenyl]-5-benzofuranyl]methyl]-3-butyl-1-(2,2,2-trifluoroethyl)-1H-pyrazole-5-methanol A solution of the product of Example 4a (0.2 g) in a mixture of THF (20 ml), conc. hydrochloric acid (3 ml) and water (3 ml) was hydrogenated over 5% palladium on carbon (0.08 g). The reaction mixture was filtered through hyflo and the solvent was removed in vacuo and the residue was purified by flash column chromatography eluting with System F (500:400:20:20) to give the title compound as an off-white foam (40 mg).

T.l.c. System F (25:15:1:1) Rf 0.3

| Assay found: | C,52.7; H,4.1; N,14.0; |
|---|---|
| C$_{26}$H$_{24}$BrF$_3$N$_6$O$_2$ requires: | C,53.0; H,4.1; N,14.3% |

Example 6

4-[[3-Bromo-2-[2-(1H-tetrazol-5-yl)phenyl]-5-benzofuranyl]methyl]-3-butyl-1-(2,2,2-trifluoroethyl)-1H-pyrazole-5-carboxaldehyde A mixture of the product of Example 5 (0.55 g), 4Å molecular sieves (powdered) (2.5 g), N-methylmorpholine-N-oxide (0.65 g) in a mixture of dry dichloromethane (10 ml) and dry acetonitrile (10 ml) was treated with tetrapropylammonium perruthenate (40 mg) at 0°. The mixture was stirred at 0° to ambient temperature for 1.5 h and filtered through "hyflo", and the solvent was evaporated. The residue was purified by flash column chromatography eluting with System F (400:400:10:10) to give a residue which was dissolved in a mixture of dichloromethane:ethyl acetate (2:1;25 ml) and washed with water (50 ml). (The pH of the aqueous solution was adjusted to 4 with aqueous sodium carbonate (2N)). The organic phase was, dried, filtered and evaporated to give the title compound as an off-white solid (0.31 g).

T.l.c. System F (25:25:1:1) Rf 0.3 n.m.r. (250 MHz; CDCl$_3$)δ0.9 (3H,t), 1.3–1.4 (2H,m), 1.52–1.66 (2H,m), 2.6 (2H,m), 4.21(2H,s), 5.2 (2H,q), 7.11 (1H,m), 7.3 (1H,d), 7.4 (1H,d), 7.65 (2H,m), 7.86–7.96 (2H,m), 9.89 (1H,s).

Example 7

4-[[3-Bromo-2-[2-(1H-tetrazol-5-yl)phenyl]-5-benzofuranyl]methyl]-3-butyl-1-(2,2,2-trifluoroethyl)-1H-pyrazole-5-carboxylic acid A solution of the product of Example 6 (0.3 g) and 2-methyl-but-2-ene (2M in THF; 4 ml) in a mixture of THF (14 ml) and t-butanol (14 ml) was treated with a solution of sodium chlorite (80% tech. 0.55 g), and sodium dihydrogenorthophosphate (0.65 g) in water (10 ml). The mixture was stirred at ambient temperature for 2 h. The solvent was removed in vacuo and the aqueous residue acidified (pH 4.5) with hydrochloric acid (2M). The product was extracted with a mixture of dichloromethane:ethyl acetate (1:1; 25 ml) and the organic extract dried and evaporated in vacuo. The residue was crystallized from methyl acetate/hexane to give the title compound as a white solid (0.2 g), m.p. 216°–220°.

| Assay Found: | C,51.7; H,3.7; N,13.5; |
|---|---|
| C$_{26}$H$_{22}$BrF$_3$N$_6$O$_3$ requires: | C,51.75; H,3.7; N,13.9% |

Example 8

2-[5-[[5-(Aminocarbonyl)-1,3-diethyl-1H-pyrazol-4-yl]methyl]-3-bromo-2-benzofuranyl]benzoic acid Trifluoroacetic acid (1 ml) was added to a solution of Intermediate 25 (0.4 g) in dry dichloromethane (3 ml) at 0° under nitrogen. The mixture was stirred at room temperature for 16 h. The solvent was evaporated and the residue purified by flash column chromatography eluting with System G (160:40:1) to give a colourless solid (303 mg) which was recrystallised from methyl acetate/ether to give the title compound as a colourless solid (188 mg), m.p. 171°–172°.

T.l.c. System G (5:5:1) Rf 0.25

Similarly prepared was:

Example 9

4-[[3-Bromo-2-(2-carboxyphenyl)-5-benzofuranyl]methyl]-1,3-diethyl-1H-pyrazole-5-carboxylic acid was prepared as a colourless solid (202 mg) m.p. 119°–125° C., by adding trifluoroacetic acid (0.5 ml) to a solution of Intermediate 24 (0.35 g) in dry dichloromethane (5 ml).

T.l.c. System G (5:5:1) Rf 0.3

Example 10

1-Butyl-3-ethyl-4-[[3-bromo-2-[2-[[(trifluoromethyl)-sulphonyl]amino]phenyl]-5-benzofuranyl]methyl]-1H-pyrazole-5-carboxaldehyde Trifluoromethanesulphonic anhydride (0.8 ml) in dry dichloromethane (2 ml) was slowly added to a stirred solution of Intermediate 29, (2.3 g) and triethylamine (0.73 ml) in dry dichloromethane (23 ml), under nitrogen, at −65° to −70°. The solution was stirred for a further 20 min at −70° C. Water (20 ml) was added and the mixture allowed to warm to room temperature. The two layers were separated and the organic phase washed with water (3×40 ml), then dried and concentrated in vacuo. The residue was purified by column chromatography (alumina, 100 g, 4.5% water) eluting with ether→ether −2% acetic acid, and then further purified by column chromatography eluting with System B (1:3) to afford the title compound, (2.2 g) as a white foam.

T.l.c. System B (1:3) Rf=0.19

| Assay found: | C,51.0; H,4.4; N,6.7; |
|---|---|
| C$_{26}$H$_{27}$BrF$_3$N$_3$O$_4$S requires: | C,50.8; H,4.4; N,6.8% |

Example 11

1-Butyl-3-ethyl-4-[[3-bromo-2-[2-[[(trifluoromethyl)sulphonyl]amino]phenyl]-5-benzofuranyl]methyl]-1H-pyrazole-5-carboxylic acid A solution of sodium chlorite (3.7 g) and sodium dihydrogenorthophosphate (3.7 g) in water (40 ml) was added to a mixture of the product of Example 10 (2.0 g), THF (40 ml), tert-butanol (40 ml) and 2-methyl-2-butene (2M solution in THF; 19.5 ml). The mixture was stirred vigorously at room temperature for 18 h. Saturated ammonium chloride solution (200 ml) was added and the mixture extracted with ethyl acetate (3×120 ml). The combined organic extracts were dried and concentrated in vacuo to afford a pale yellow gum. This was purified by flash column chromatography, eluting with System B (1:4) with 1% acetic acid to afford the title compound, (1.50 g) as a white solid.

T.l.c. System B (1:1) Rf=0.44 n.m.r. (250 MHz; $CDCl_3$)δ0.92 (3H,t), 1.15 (3H,t), 1.32 (2H,m), 1.81 (2H,m), 2.59 (2H,q), 4.26 (2H,s), 4.55 (2H,t), 7.20 (1H,dd), 7.31 (1H,d), 7.40 (1H,d), 7.42 (1H,ddd), 7.52 (1H,ddd), 7.68 (1H,dd), 7.71 (1H,brs), 7.82 (1H,dd).

Example 12

5-[2-[3-Bromo-5-[[3-butyl-5-(methoxymethyl)-1H-pyrazole-4-yl]methyl]-2-benzofuranyl]phenyl]-1H-tetrazole Conc. HCl (0.15 ml) was added to a solution of Intermediate 30 (170 mg) in methanol/THF (3:1; 4 ml) at room temperature under nitrogen and the mixture stirred for 2 h. The solvent was evaporated and the residue purified by flash column chromatography eluting with ethyl acetate gave the title compound as a colourless foam (80 mg).

T.l.c. ethyl acetate Rf 0.25 streaking to 0.1 n.m.r. (250 MHz; $CDCl_3$)δ: 0.82 (t,3H), 1.25 (m,2H), 1.45 (m,2H), 2.41 (m,2H), 3.19 (s,3H), 3.86 (s,2H), 4.15 (s,2H), 7.07-7.21 (m,3H), 7.42 (brs,2H), 7.65 (m,2H), 7.89 (m,1H), 8.07 (m,1H).

Example 13

1-Butyl-3-ethyl-4-[[3-bromo-2-[2-[[(trifluoromethyl)sulphonyl]amino]phenyl]-5-benzofuranyl]methyl]-1H-pyrazole-5-methanol Trifluoromethanesulphonic anhydride (1M solution in dichloromethane; 1 ml) was added dropwise to a stirred solution of Intermediate 28 (500 mg), triethylamine (0.15 ml) and dichloromethane (10 ml) at −70° C. under nitrogen. The solution was stirred at −70° C. for 1 h, water (15 ml) was added and the mixture allowed to warm to room temperature. The organic phase was separated, washed with water (3×15 ml), dried and concentrated in vacuo. The residue was purified by flash column chromatography [alumina 4.5% water, 40 g] eluting with ether, then ether-1% acetic acid, then further purified by flash column chromatography eluting with System D (20:1) to afford the title compound (150 mg), as a white foam.

T.l.c. System D (92:8) Rf=0.18

| Assay Found: | C,51.0; H,4.4; N,6.7; |
|---|---|
| $C_{26}H_{27}BrF_3N_3O_4S$ requires: | C,50.8; H,4.4; N,6.8% |

The compounds of the invention are tested in vitro for angiotensin II antagonism. Aortic strips are obtained from male New Zealand white rabbits and prepared for recording isometric contractions in response to cumulative addition of angiotensin II. The potencies of test antagonists are assessed by measuring their abilities to displace the angiotensin II cumulative concentration response curve. The method used is that of Ackerly et al., Proc. Natl. Acad. Sci., 74(12), pp5725-28 (1977) with the exception that the final composition of the physiological salt solution is as given below in Table 1:

TABLE 1

| Ingredient | Amount (mM) |
|---|---|
| $Na^+$ | 143.4 |
| $K^+$ | 5.9 |
| $Mg^{2+}$ | 0.6 |
| $Ca^{2+}$ | 1.3 |
| $Cl^-$ | 124.5 |
| $HPO_4^-$ | 1.2 |
| $SO_4^{2-}$ | 0.6 |
| $HCO_3^-$ | 25.0 |
| glucose | 11.1 |
| indomethacin | 0.005 |
| ascorbic acid | 0.1 |

The tissues are initially challenged with $K^+$ (80 mM) and then washed at 0, 5, 10 and 15 minutes after the response to $K^+$ has plateaued. After a further 45 minutes an angiotensin II cumulative response curve is constructed (0.1 nM to 0.1 μM in 10-fold increments) and the tissues are washed as before. A second, third and fourth angiotensin II cumulative response curve (0.1 nM to 0.1 μM in 3-fold increments) is then constructed at hourly intervals (15 minutes washing after each curve followed by 45 minutes equilibration). The compounds of the invention (38 μM) are tested for angiotensin II antagonism by application 45 minutes before construction of the fourth angiotensin II curve. The third and fourth angiotensin II curves are expressed graphically and a concentration ratio (CR) is calculated by dividing the angiotensin II $EC_{50}$ value obtained in the presence of the test antagonist (i.e. fourth curve) by the angiotensin II $EC_{50}$ value obtained in the absence of the test antagonist (i.e. third curve).

The potency of the test antagonist is expressed as a pKb which is calculated from the equation:

$$pKb = -\log \left[ \frac{CR - 1}{[\text{antagonist}]} \right]$$

which is a rearrangement of equation 4 described by Furchgott, in Handbook of Exp. Pharmacol., 33, p290 (1972) (eds. Blaschko and muscholl).

If a compound supresses the maximum response to angiotensin II, a pKb is estimated using the double reciprocal plot technique for insurmountable antagonists, described by T. P. Kenakin, Pharmacol. Rev., 36(3), pp165-222 (esp. 203-204) (1984).

Compounds of the invention will desirably exhibit a pKb in the range between 5 and 12. Thus we have found that the compounds of the invention inhibit the action of the hormone angiotensin II and are therefore useful in the treatment of conditions in which it is desirable to inhibit angiotensin II activity. In particular, the compounds of Examples are active in the above test.

There is thus provided as a further aspect of the invention a compound of general formula (I) or a physiologically acceptable salt, solvate or metabolically labile ester thereof for use in the treatment of conditions associated with excessive or unregulated angiotensin II activity.

In a further or alternative aspect of the invention there is provided a compound of general formula (I) or a physiologically acceptable salt, solvate or metabolically labile ester thereof for the manufacture of a therapeutic agent for the treatment of conditions associated with excessive or unregulated angiotensin II activity.

There is also provided in a further or alternative aspect of the invention a method for the treatment of conditions associated with excessive or unregulated angiotensin II activity in a mammal including man comprising administration of an effective amount to a mammal in need of such treatment a compound of general formula (I) or a physiologically acceptable salt, solvate or metabolically labile ester thereof.

In addition, by virtue of their antagonistic activity at angiotensin II receptors, compounds of the present invention will be of value in the treatment of conditions associated with activation of the Renin-Angiotensin System.

There is thus provided, in a further aspect of the present invention, a compound of general formula (I) or a physiologically acceptable salt, solvate or metabolically labile ester thereof for use in the treatment of a condition associated with activation of the Renin-Angiotensin system.

In a further or alternative aspect of the present invention there is provided a compound of general formula (I) or a physiologically acceptable salt, solvate or metabolically labile ester thereof for the manufacture of a therapeutic agent for the treatment of a condition associated with activation of the Renin-Angiotensin System.

There is also provided in a further or alternative aspect of the present invention a method for the treatment of a condition associated with the activation of the Renin-Angiotensin System in a mammal including man comprising administration of an effective amount to a mammal in need of such treatment of a compound of general formula (I) or a physiologically acceptable salt, solvate or metabolically labile ester thereof.

The following examples illustrate pharmaceutical formulations according to the invention. The term "active ingredient" is used herein to represent a compound of formula (I).

Pharmaceutical Example 1

| Oral Tablet A | |
| --- | --- |
| Active Ingredient | 700 mg |
| Sodium starch glycollate | 10 mg |
| Microcrystalline cellulose | 50 mg |
| Magnesium stearate | 4 mg |

Sieve the active ingredient and microcrystalline cellulose through a 40 mesh screen and blend in a appropriate blender. Sieve the sodium starch glycollate and magnesium stearate through a 60 mesh screen, add to the powder blend and blend until homogeneous. Compress with appropriate punches in an automatic tablet press. The tablets may be coated with a thin polymer coat applied by the film coating techniques well known to those skilled in the art. Pigments may be incorporated in the film coat.

Pharmaceutical Example 2

| Oral Tablet B | |
| --- | --- |
| Active Ingredient | 500 mg |
| Lactose | 100 mg |
| Maize Starch | 50 mg |
| Polyvinyl pyrrolidone | 3 mg |
| Sodium starch glycollate | 10 mg |
| Magnesium stearate | 4 mg |
| Tablet Weight | 667 mg |

Sieve the active ingredient, lactose and maize starch through a 40 mesh screen and blend the powders in a suitable blender. Make an aqueous solution of the polyvinyl pyrrolidone (5–10% w/v). Add this solution to the blended powders and mix until granulated; pass the granulate through a 12 mesh screen and dry the granules in a suitable oven or fluid bed dryer. Sieve the remaining components through a 60 mesh screen and blend them with the dried granules. Compress, using appropriate punches, on an automatic tablet press.

The tablets may be coated with a thin polymer coat applied by film coating techniques well known to those skilled in art. Pigments may be incorporated in the film coat.

Pharmaceutical Example 3

| Inhalation Cartridge | |
| --- | --- |
| Active Ingredient | 1 mg |
| Lactose | 24 mg |

Blend active ingredient, particle size reduced to a very fine particle size (weight mean diameter ca. 5 $\mu M$) with the lactose in a suitable powder blender and fill the powder blender into No. 3 hard gelatin capsules.

The contents of the cartridges may be administered using a powder inhaler.

Pharmaceutical Example 4

| Injection Formulation | % w/v |
| --- | --- |
| Active ingredient | 1.00 |
| Water for injections B.P. to | 100.00 |

Sodium chloride may be added to adjust the tonicity of the solution and the pH may be adjusted to that of maximum stability and/or to facilitate solution of the active ingredient using dilute acid or alkali or by the addition of suitable buffer salts. Antioxidants and metal chelating salts may also be included.

The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

We claim:

1. A compound of formula (I):

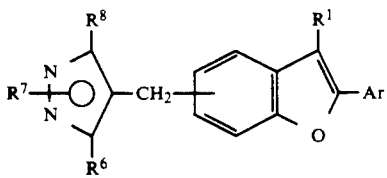

or a physiologically acceptable salt, solvate or metabolically labile ester thereof wherein $R^1$ represents a hydrogen atom or a halogen atom or a group selected from $C_{1-6}$alkyl, $C_{2-6}$alkenyl, fluoro$C_{1-6}$alkyl, $C_{1-6}$alkoxy —CHO, —CO$_2$H or —COR$^2$;

Ar represents the group

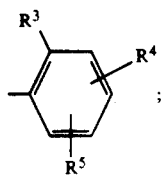

$R^2$ represents a group selected from $C_{1-6}$alkyl, $C_{2-6}$alkenyl, $C_{1-6}$alkoxy or the group —NR$^{14}$R$^{15}$;

$R^3$ represents a group selected from —CO$_2$H, —NHSO$_2$CF$_3$ or a C-linked tetrazolyl group;

$R^4$ and $R^5$ which may be the same or different each independently represent a hydrogen atom or a halogen atom or a $C_{1-6}$alkyl group;

$R^6$ represents a hydrogen atom or a group selected from $C_{1-6}$alkyl or $C_{2-6}$alkenyl, $C_{1-6}$alkylthio, $C_{1-6}$alkoxy, $C_{3-7}$cycloalkyl or $C_{3-7}$cycloalkyl$C_{1-4}$alkyl;

$R^7$ represents a hydrogen atom or a group selected from $C_{1-6}$alkyl, $C_{3-7}$cycloalkyl, $C_{3-7}$cycloalkyl$C_{1-4}$alkyl, $C_{3-6}$alkenyl, fluoro$C_{1-6}$alkyl, fluoro$C_{3-6}$alkenyl, phenyl, —(CH$_2$)$_k$COR$^9$ or —(CH$_2$)$_k$SO$_2$R$^9$;

$R^8$ represents a hydrogen atom or a group selected from $C_{1-6}$alkyl optionally substituted by a hydroxy or $C_{1-6}$alkoxy group, $C_{2-6}$alkenyl, fluoro$C_{1-6}$alkyl, —(CH$_2$)$_m$R$^{10}$, —(CH$_2$)$_n$COR$^{11}$ or —(CH$_2$)$_p$NR$^{12}$COR$^{13}$;

$R^9$ represents a group selected from $C_{1-6}$alkyl, $C_{2-6}$alkenyl, $C_{1-6}$alkoxy or the group —NR$^{14}$R$^{15}$;

$R^{10}$ represents a phenoxy or benzyloxy group;

$R^{11}$ represents a hydrogen atom or a group selected from hydroxy, $C_{1-6}$alkyl, $C_{1-6}$alkoxy, phenyl, phenoxy or the group —NR$^{14}$R$^{15}$;

$R^{12}$ represents a hydrogen atom or a $C_{1-6}$alkyl group;

$R^{13}$ represents a hydrogen atom or a group selected from $C_{1-6}$alkyl, $C_{1-6}$alkoxy, phenyl, benzyl, phenoxy or the group —NR$^{14}$R$^{15}$;

$R^{14}$ and $R^{15}$, which may be the same or different, each independently represent a hydrogen atom or a $C_{1-4}$alkyl group or —NR$^{14}$R$^{15}$ forms a saturated heterocyclic ring which has 5 or 6 ring members and may optionally contain in the ring one oxygen atom;

k represents zero or an integer from 1 to 4;
m represents an integer from 1 to 4;
n represents zero or an integer from 1 to 4; and
p represents an integer from 1 to 4.

2. A compound according to claim 1 wherein $R^6$ represents a hydrogen atom or a $C_{1-5}$alkyl or a $C_{3-5}$alkenyl group.

3. A compound according to claim 1 wherein the group $R^7$ is adjacent to the group $R^8$.

4. A compound according to claim 1 wherein the group Het-CH$_2$- is attached at the 5- or 6-position on the benzofuran ring.

5. A compound according to claim 1 wherein $R^4$ and $R^5$ each independently represent a hydrogen atom or a halogen atom.

6. A compound according to claim 2 wherein $R^6$ is a $C_{2-4}$alkyl group.

7. A compound according to claim 6 wherein $R^6$ is selected from the group consisting of ethyl, n-propyl and n-butyl.

8. A compound according to claim 1 wherein $R^7$ is selected from the group consisting of $C_{1-6}$alkyl, $C_{3-7}$cycloalkyl, $C_{3-7}$cycloalkyl$C_{1-4}$alkyl, phenyl, fluoro$C_{1-6}$alkyl and —(CH$_2$)$_k$SO$_2$R$^9$ where R$^9$ represents the group —NR$^{14}$R$^{15}$ in which R$^{14}$ and R$^{15}$ each represent a $C_{1-4}$alkyl group and k is zero.

9. A compound according to claim 8 wherein $R^7$ is selected from the group consisting of $C_{1-5}$alkyl, $C_{3-5}$cycloalkyl, $C_{3-5}$cycloalkyl$C_{1-4}$alkyl and fluoro$C_{1-3}$alkyl.

10. A compound according to claim 9 wherein $R^7$ is selected from the group consisting of ethyl, isopropyl, isobutyl, cyclobutyl, cyclopropylmethyl and —CH$_2$CF$_3$.

11. A compound according to claim 1 wherein $R^8$ is selected from the group consisting of hydrogen, $C_{1-6}$alkyl optionally substituted by hydroxy or $C_{1-3}$alkoxy, —(CH$_2$)$_m$R$^{10}$ wherein R$^{10}$ is a benzyloxy group and m is 1 or 2, —(CH$_2$)$_n$COR$^{11}$ wherein R$^{11}$ is hydrogen, hydroxy or $C_{1-3}$alkoxy and n is zero, 1 or 2, and —(CH$_2$)$_p$NR$^{12}$COR$^{13}$ wherein R$^{12}$ is hydrogen or $C_{1-3}$alkyl, R$^{13}$ is hydrogen or $C_{1-3}$alkyl and p is 1 or 2.

12. A compound according to claim 11 wherein $R^8$ is selected from the group consisting of $C_{1-3}$alkyl optionally substituted by methoxy, and —(CH$_2$)$_n$COR$^{11}$ wherein R$^{11}$ is methoxy and n is zero or 1.

13. A compound according to claim 11 wherein $R^8$ is selected from the group consisting of —CH$_2$OH, —CH$_2$OCH$_3$, —CHO and —CO$_2$H.

14. A compound according to claim 2 wherein $R^1$ is selected from the group consisting of hydrogen, halogen, $C_{1-6}$alkyl, $C_{1-6}$alkoxy and fluoro$C_{1-6}$alkyl.

15. A compound according to claim 14 wherein $R^1$ is a bromine atom.

16. A compound according to claim 4 wherein the group Het-CH$_2$- is attached at the 5-position on the benzofuran ring.

17. A compound according to claim 1 wherein $R^4$ and $R^5$ each represent a hydrogen atom.

18. A compound which is 4-[[3-bromo-2-(2-carboxyphenyl)-5-benzofuranyl]methyl]-1,3-diethyl-1H-pyrazole-5-carboxylic acid, or a physiologically acceptable salt, solvate or metabolically labile ester thereof.

19. A compound of formula (I)

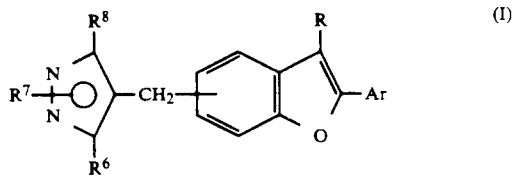

or a physiologically acceptable salt, solvate or metabolically labile ester thereof
wherein
$R^1$ represents a halogen atom;
Ar represents the group

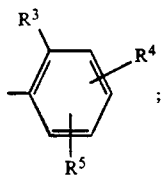

$R^3$ represents a group selected from $-CO_2H$, $-NHSO_2CF_3$ or a C-linked tetrazolyl group;
$R^4$ and $R^5$ each represents a hydrogen atom;
$R^6$ represents a $C_{1-6}$alkyl group;
$R^7$ represents a hydrogen atom or a group selected from $C_{1-6}$alkyl or fluoro$C_{1-6}$alkyl;
$R^8$ represents a group selected from $C_{1-6}$alkyl optionally substituted by a hydroxy or $C_{1-6}$alkoxy group, $-(CH_2)_m R^{10}$ or $-(CH_2)_n COR^{11}$;
$R^{10}$ represents a benzyloxy group;
$R^{11}$ represents a hydrogen atom or a group selected from hydroxy or the group $-NR^{14}R^{15}$;
$R^{14}$ and $R^{15}$ each represent a hydrogen atom;
m represents an integer from 1 to 4; and
n represents zero or an integer from 1 to 4.

20. A pharmaceutical composition comprising at least one compound of general formula (I) as defined in claim 1 or a physiologically acceptable salt, solvate or metabolically labile ester thereof, together with at least one physiologically acceptable carrier or excipient.

* * * * *